(12) United States Patent
Katayama et al.

(10) Patent No.: US 9,599,598 B2
(45) Date of Patent: Mar. 21, 2017

(54) $SO_x$ GAS SENSOR AND METHOD OF MEASURING CONCENTRATION OF $SO_x$ GAS

(71) Applicant: SHINKO ELECTRIC INDUSTRIES CO., LTD., Nagano (JP)

(72) Inventors: Ryuhei Katayama, Nagano (JP); Shigeaki Suganuma, Nagano (JP)

(73) Assignee: SHINKO ELECTRIC INDUSTRIES CO., LTD., Nagano (JP)

(*) Notice: Subject to any disclaimer, the term of this patent is extended or adjusted under 35 U.S.C. 154(b) by 359 days.

(21) Appl. No.: 14/272,694

(22) Filed: May 8, 2014

(65) Prior Publication Data

US 2014/0353174 A1    Dec. 4, 2014

(30) Foreign Application Priority Data

May 30, 2013    (JP) ................. 2013-114712

(51) Int. Cl.
  *G01N 27/409* (2006.01)
  *G01N 33/00* (2006.01)
  *G01N 27/419* (2006.01)
(52) U.S. Cl.
  CPC ....... *G01N 33/0042* (2013.01); *G01N 27/419* (2013.01)
(58) Field of Classification Search
  CPC ................ G01N 33/0042; G01N 27/419
  See application file for complete search history.

(56) References Cited

U.S. PATENT DOCUMENTS

2005/0077177 A1    4/2005  Sakayanagi
2011/0314898 A1*  12/2011  Liemersdorf ........ G01N 27/419
                                                       73/23.31

FOREIGN PATENT DOCUMENTS

EP    1582865    10/2005
EP    2369331    9/2011
(Continued)

OTHER PUBLICATIONS

Machine English translation of JP H05-023544, No Date.*
(Continued)

*Primary Examiner* — Julie Tavares
(74) *Attorney, Agent, or Firm* — IPUSA, PLLC

(57) ABSTRACT

An $SO_x$ gas sensor includes a first solid electrolyte member composing a part of a wall of a gas reduction chamber and provided with a first gas introducing hole for introducing sample gas into the gas reduction chamber, an oxidation part for oxidizing noise gas other than the $SO_x$ gas in the sample gas, and a reduction mechanism for reducing the $SO_x$ gas in the sample gas, in the gas reduction chamber; a communication unit provided with a second gas introducing hole for introducing the sample gas into a gas measurement chamber from the gas reduction chamber; and a second solid electrolyte member composing a part of a wall of the gas measurement chamber and provided with an oxidation mechanism for oxidizing the $SO_x$ gas, and a measurement mechanism for measuring the concentration of the $SO_x$ gas, in the gas measurement chamber.

8 Claims, 1 Drawing Sheet

(56) References Cited

FOREIGN PATENT DOCUMENTS

| | | |
|---|---|---|
| JP | H05-023544 | 2/1993 |
| JP | 07-103937 | 4/1995 |
| JP | 11-190719 | 7/1999 |
| JP | 11-352096 | 12/1999 |
| JP | 2003-149199 | 5/2003 |

OTHER PUBLICATIONS

Extended European Search Report dated Oct. 20, 2014 issued with respect to the corresponding European Patent Application No. 14168394.6.

\* cited by examiner

$SO_x$ GAS SENSOR AND METHOD OF MEASURING CONCENTRATION OF $SO_x$ GAS

CROSS-REFERENCE TO RELATED APPLICATION

The present application is based on and claims the benefit of priority of Japanese Priority Application No. 2013-114712 filed on May 30, 2013, the entire contents of which are hereby incorporated by reference.

BACKGROUND OF THE INVENTION

1. Field of the Invention

The present invention relates to an $SO_x$ gas sensor and a method of measuring concentration of $SO_x$ gas.

2. Description of the Related Art

Conventionally, an $SO_x$ gas sensor using a solid electrolyte material has been studied.

For example, Patent Document 1 discloses a gas sensor for detecting $SO_x$ gas in which a sub electrode of sulfate is provided on a base material composed of a solid electrolyte material. The gas sensor has a structure in which a mixed body of sulfate including silver sulfate is used as the sulfate of the sub electrode, a metal electrode including silver is provided on a surface of the sub electrode, and a platinum film is provided to cover a surface of the metal electrode.

However, it was necessary to further improve thermal stability of the gas sensor disclosed in Patent Document 1, because silver sulfate used for the sub electrode easily decomposes, as a result, thermal decomposition gradually occurs at 600° C., which is an operating temperature of the gas sensor. Further, it was also necessary to improve chemical stability of the gas sensor disclosed in Patent Document 1. Although an $SO_x$ gas sensor is often used for measuring components in exhaust gas (flue gas), the exhaust gas includes various accompanying components which can poison silver sulfate.

Patent Document

[Patent Document 1] Japanese Laid-open Patent Publication No. H7-103937

SUMMARY OF THE INVENTION

The present invention is made in light of the above problems, and provides an $SO_x$ gas sensor that is thermally and chemically stable.

According to an embodiment, there is provided an $SO_x$ gas sensor including a gas reduction chamber in which $SO_x$ gas included in sample gas is reduced; a gas measurement chamber in which the concentration of the $SO_x$ gas included in the sample gas is measured while the $SO_x$ gas is being oxidized; a first solid electrolyte member composing a part of a wall of the gas reduction chamber and provided with a first gas introducing hole for introducing the sample gas into the gas reduction chamber, an oxidation part provided in the first gas introducing hole for oxidizing noise gas other than the $SO_x$ gas included in the sample gas, and a reduction mechanism for reducing the $SO_x$ gas included in the sample gas, in the gas reduction chamber; a communication unit provided between the gas reduction chamber and the gas measurement chamber to partition the gas reduction chamber and the gas measurement chamber and provided with a second gas introducing hole for introducing the sample gas into the gas measurement chamber from the gas reduction chamber, and a gas diffusion resistor provided in the second gas introducing hole; and a second solid electrolyte member composing a part of a wall of the gas measurement chamber and provided with an oxidation mechanism for oxidizing the $SO_x$ gas included in the sample gas, in the gas measurement chamber, and a measurement mechanism for measuring the concentration of the $SO_x$ gas included in the sample gas introduced into the gas measurement chamber.

According to another embodiment, there is provided a method of measuring concentration of $SO_x$ gas included in sample gas, including an oxidation step of oxidizing noise gas other than the $SO_x$ gas included in the sample gas; a first supplying step of supplying the sample gas after the oxidation step, into a gas reduction chamber; a reduction step of reducing the $SO_x$ gas included in the sample gas in the gas reduction chamber while exhausting oxygen in the gas reduction chamber to outside the gas reduction chamber; a second supplying step of supplying the sample gas after the reduction step, into a gas measurement chamber from the gas reduction chamber through a gas diffusion resistor; and a measuring step of measuring variation of a current value of current that flows through a solid electrolyte that composes a part of a wall of the gas measurement chamber or variation of a resistance value of the solid electrolyte, while supplying oxygen ion into the gas measurement chamber through the solid electrolyte and oxidizing $SO_2$ gas included in the sample gas to $SO_3$ gas in the gas measurement chamber.

Note that also arbitrary combinations of the above-described elements, and any changes of expressions in the present invention, made among methods, devices, systems and so forth, are valid as embodiments of the present invention.

BRIEF DESCRIPTION OF THE DRAWINGS

Other objects, features and advantages of the present invention will become more apparent from the following detailed description when read in conjunction with the accompanying drawings.

DETAILED DESCRIPTION OF THE PREFERRED EMBODIMENTS

Figure 1A:
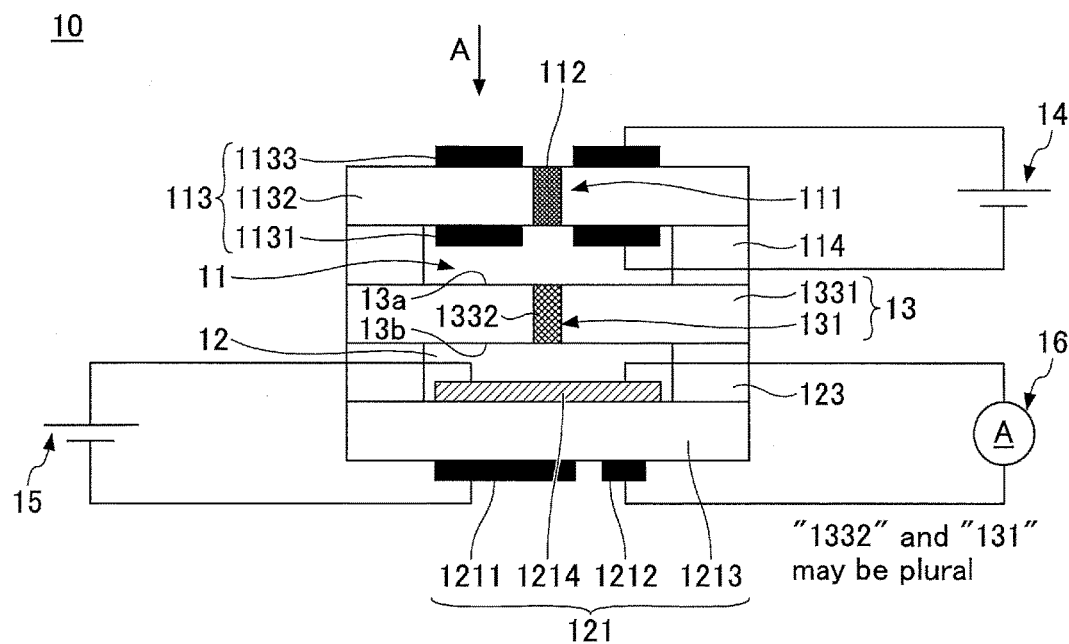
FIG. 1A is a cross sectional view illustrating an example of an $SO_x$ gas sensor of an embodiment.

The invention will be described herein with reference to illustrative embodiments. Those skilled in the art will recognize that many alternative embodiments can be accomplished using the teachings of the present invention and that the invention is not limited to the embodiments illustrated for explanatory purposes.

It is to be noted that, in the explanation of the drawings, the same components are given the same reference numerals, and explanations are not repeated.

An example of an $SO_x$ gas sensor of the embodiment is explained.

The $SO_x$ gas sensor of the embodiment includes a gas reduction chamber in which $SO_x$ gas included in sample gas is reduced, a gas measurement chamber in which the concentration of the $SO_x$ gas included in the sample gas is measured while the $SO_x$ gas is being oxidized and a communication unit that is provided between the gas reduction chamber and the gas measurement chamber to partition the gas reduction chamber and the gas measurement chamber.

The $SO_x$ gas sensor of the embodiment further includes a first solid electrolyte member that composes a part of a wall of the gas reduction chamber. The first solid electrolyte member is provided with a first gas introducing hole for introducing the sample gas into the gas reduction chamber, an oxidation part for oxidizing noise gas (contaminant gas) other than the $SO_x$ gas included in the sample and a reduction mechanism for reducing the $SO_x$ gas included in the sample gas, in the gas reduction chamber. Here, the oxidation part is provided such that the sample gas is introduced into the gas reduction chamber after the noise gas is oxidized by the oxidation part.

The communication unit is provided with a second gas introducing hole for introducing the sample gas into the gas measurement chamber from the gas reduction chamber and a gas diffusion resistor provided in the second gas introducing hole.

The $SO_x$ gas sensor of the embodiment further includes a second solid electrolyte member that composes a part of a wall of the gas measurement chamber. The second solid electrolyte member is provided with an oxidation mechanism for oxidizing the $SO_x$ gas included in the sample gas, in the gas measurement chamber, and a measurement mechanism for measuring the concentration of the $SO_x$ gas included in the sample gas introduced into the gas measurement chamber.

In the following, the first solid electrolyte substrate and the first wall portion are an example of a first solid electrolyte member, and the second solid electrolyte substrate and the second wall portion are an example of a second solid electrolyte member.

An example of a specific structure of the $SO_x$ gas sensor of the embodiment is explained with reference to drawings.

Figure 1B:
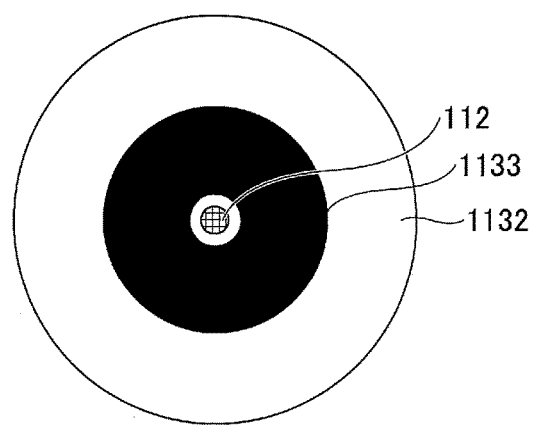
FIG. 1B is a top view of the $SO_x$ gas sensor of the embodiment.

FIG. 1A is a cross sectional view illustrating an example of a $SO_x$ gas sensor 10 of the embodiment. FIG. 1B is a top view of the $SO_x$ gas sensor 10 of the embodiment and corresponds to a view seen in a direction indicated by an arrow "A" in FIG. 1A.

As illustrated in FIG. 1A, the $SO_x$ gas sensor 10 includes a first solid electrolyte substrate 113, a first wall portion 114, a communication unit 13, a second wall portion 123 and a second solid electrolyte substrate 121, provided in this order. Further, the $SO_x$ gas sensor 10 includes a gas reduction chamber 11 and a gas measurement chamber 12 that communicates with the gas reduction chamber 11 via the communication unit 13. Further, a first power source (voltage applying unit) 14, a second power source (voltage applying unit) 15 and an ampere meter 16 (resistance measurement unit) are connected to the $SO_x$ gas sensor 10.

The first solid electrolyte substrate 113 includes a first solid electrolyte 1132, a first electrode 1133, a second electrode 1131 and an oxidation part 112. The first electrode 1133 and the second electrode 1131 are provided at one surface (upper surface in FIG. 1A) and another surface (lower surface in FIG. 1A) of the first solid electrolyte 1132, respectively. The second electrode 1131 is provided in the gas reduction chamber 11. The first solid electrolyte 1132, the first electrode 1133 and the second electrode 1131 configured as such can function as a reduction mechanism for reducing the $SO_x$ gas included in the sample gas, in the gas reduction chamber 11, as will be explained later in detail.

The first solid electrolyte substrate 113 is provided with a first gas introducing hole 111 through which the sample gas is introduced into the gas reduction chamber 11. In this embodiment, the oxidation part 112 that oxidizes the $SO_x$ gas included in the sample gas is provided in the first gas introducing hole 111. The structure of the oxidation part 112 is explained later in detail.

The communication unit 13 includes a substrate 1331 provided with a second gas introducing hole 1332 that penetrates the substrate 1331 and a gas diffusion resistor 131 provided in the second gas introducing hole 1332.

The second solid electrolyte substrate 121 includes a second solid electrolyte 1213, a third electrode (measurement electrode) 1214, a fourth electrode 1211 and a measurement electrode 1212. The third electrode 1214 is provided at one surface (upper surface in FIG. 1A) of the second solid electrolyte 1213. The third electrode 1214 is provided in the gas measurement chamber 12. The fourth electrode 1211 and a measurement electrode 1212 are provided at another surface (lower surface in FIG. 1A) of the second solid electrolyte 1213.

The second solid electrolyte 1213, the third electrode 1214 and the fourth electrode 1211 configured as such can function as an oxidation mechanism for oxidizing the $SO_x$ gas included in the sample gas, in the gas measurement chamber 12, as will be explained later in detail. Further, the second solid electrolyte 1213, the third electrode 1214, and the measurement electrode 1212 configured as such can function as a measurement mechanism for measuring the concentration of the $SO_x$ gas included in the sample gas introduced into the gas measurement chamber 12, as will be explained later in detail.

The gas reduction chamber 11 is formed (surrounded) by the first solid electrolyte 1132, the first wall portion 114 and the substrate 1331 of the communication unit 13. The first wall portion 114 is bonded to the other surface of the first solid electrolyte 1132 and bonded to a first surface 13a (upper surface in FIG. 1A) of the substrate 1331 of the communication unit 13. Thus, the gas reduction chamber 11 is formed in an open portion of the first wall portion 114.

The gas measurement chamber 12 is formed (surrounded) by the substrate 1331 of the communication unit 13, the second wall portion 123 and the second solid electrolyte 1213. The second wall portion 123 is bonded to a second surface 13b (lower surface in FIG. 1A) of the substrate 1331 and bonded to the one surface of the second solid electrolyte 1213. Thus, the gas measurement chamber 12 is formed in an open portion of the second wall portion 123.

Thus, the gas reduction chamber 11 and the gas measurement chamber 12 are provided at the first surface 13a side and the second surface 13b side of the substrate 1331 of the communication unit 13.

Next, each component is explained in detail.
(First Solid Electrolyte Substrate 113 and Gas Reduction Chamber 11)

The first gas introducing hole 111 is an open portion for introducing the sample gas into the gas reduction chamber 11. Shape or size of the first gas introducing hole 111 is not particularly limited as long as the sample gas can be introduced into the gas reduction chamber 11.

For example, the first gas introducing hole 111 may be a cylindrical open portion that penetrates the first solid electrolyte 1132 and is provided at a center (center portion) of the first solid electrolyte 1132. The number of the first gas introducing hole 111 may be one or more.

Specifically, for example, when the $SO_x$ gas sensor 10 has a columnar shape as illustrated in FIG. 1B, the first gas introducing hole 111 may be a cylindrical open portion that penetrates the first solid electrolyte 1132 on a center axis of the $SO_x$ gas sensor 10.

The oxidation part 112 that oxidizes the sample gas may be provided in the first gas introducing hole 111. In this embodiment, as will be described later, concentration of the $SO_2$ gas (sulfur dioxide) is measured by using a mechanism of oxidizing the $SO_2$ gas included in the sample gas in the gas measurement chamber 12. Thus, by previously oxidizing and removing the noise gasses other than $SO_2$ such as hydrogen, carbon monoxide or the like that may be included in the sample gas, by the oxidation part 112, influence of the noise gasses in the gas measurement chamber 12 can be reduced.

A specific structure of the oxidation part 112 is not particularly limited, but may include one or more material selected from metal, alloy and oxide including one or more oxidation catalyst selected from a group including platinum, rhodium, ruthenium and palladium. Further, in this embodiment, the oxidation part 112 may include a porous ceramics and the above described one or more material may be supported at a surface and inside the porous ceramics. At this time, the movement of the gasses flowing through the oxidation part 112 in the first gas introducing hole 111 is regulated by the function of the porous ceramics.

The first solid electrolyte 1132 is capable of exhausting oxygen in the gas reduction chamber 11 to outside the gas reduction chamber 11 and also capable of generating pump current therein. The first solid electrolyte 1132 is an oxygen ion conductive solid electrolyte. The first solid electrolyte 1132 is not particularly limited, but yttria-stabilized zirconia, calcia-stabilized zirconia, samarium-doped ceria or the like may be used, for example. Yttria-stabilized zirconia may be preferably used in view of oxygen ion conductivity and mechanical strength.

The power source 14 is connected to the first electrode 1133 and the second electrode 1131. Specifically, in this embodiment, a positive electrode of the power source 14 is connected to the first electrode 1133 and a negative electrode of the power source 14 is connected to the second electrode 1131, respectively. When voltage is applied to the first electrode 1133 and the second electrode 1131 by the power source 14, oxygen in the gas reduction chamber 11 is exhausted to outside the gas reduction chamber 11 through the first solid electrolyte 1132. Then, a reduction process of $SO_x$ gas is performed in the gas reduction chamber 11. Specifically, by this reduction process, $SO_3$ gas included in the $SO_x$ gas is reduced to $SO_2$ gas in accordance with a reaction of the following equation 1.

$$2SO_3 \rightarrow 2SO_2 + O_2 \quad \text{(Equation 1)}$$

As the $SO_x$ gas includes the $SO_2$ gas and the $SO_3$ gas, if oxygen partial pressure in atmosphere of the gas reduction chamber 11 is lowered, the above equilibrium moves to the $SO_2$ gas side. In other words, the $SO_2$ gas can be easily reduced in low oxygen atmosphere. According to the embodiment, by using the oxygen ion conductive solid electrolyte as the first solid electrolyte 1132 as described, oxygen in the gas reduction chamber 11 can be removed and the $SO_3$ gas can be selectively reduced to the $SO_2$ gas.

Structures of the first electrode 1133 and the second electrode 1131 are not particularly limited, however, at least the second electrode 1131 may be composed of metal capable of ionizing oxygen when voltage is being applied. For such metal, one or more metal selected from a group including platinum, palladium and iridium may be used, for example.

The first electrode 1133 and the second electrode 1131 may be composed of one or more metal selected from a group including platinum, palladium and iridium.

Shapes of the first electrode 1133 and the second electrode 1131 are not particularly limited, however, for example, when the $SO_x$ gas sensor 10 has a circular shape as illustrated in FIG. 1B, the first electrode 1133 and the second electrode 1131 may have a circular shape, respectively, in accordance with the shape of the $SO_x$ gas sensor 10. In this case, as illustrated in FIG. 1B, the first electrode 1133 and the second electrode 1131 may be provided with opening portions, respectively, in accordance with the position and the size of the first gas introducing hole 111. Further, as illustrated in FIG. 1B, for example, the first electrode 1133 and the second electrode 1131 may be concentrically provided with the first gas introducing hole 111.

(Communication Unit 13)

The communication unit 13 is positioned between the gas reduction chamber 11 and the gas measurement chamber 12 and is configured to regulate movement of gasses in the gas reduction chamber 11 and the gas measurement chamber 12 therebetween.

The second gas introducing hole 1332 is an open portion provided in the substrate 1331 of the communication unit 13 through which the $SO_2$ gas generated by the reduction process in the gas reduction chamber 11 flows into the gas measurement chamber 12. Shape or size of the second gas introducing hole 1332 is not particularly limited as long as the sample gas can be introduced into the gas measurement chamber 12, as similar to the first gas introducing hole 111.

For example, the second gas introducing hole 1332 may be a cylindrical open portion that penetrates the communication unit 13 and is provided at a center (center portion) of the communication unit 13. Then, the gas diffusion resistor 131 may be provided in the second gas introducing hole 1332. Thus, the $SO_2$ gas generated by the reduction process in the gas reduction chamber 11 flows into the gas measurement chamber 12 through the gas diffusion resistor 131. The number of the second gas introducing hole 1332 may be one or more.

A specific structure of the gas diffusion resistor 131 is not particularly limited, but may be composed of a porous ceramics. At this time, different from the oxidation part 112, the gas diffusion resistor 131 does not include the one or more material selected from metal, alloy and oxide including one or more oxidation catalyst.

Alternatively, the substrate 1331 of the communication unit 13 may be provided with a plurality of the second gas introducing holes 1332 and the gas diffusion resistor 131 may be provided in each of the second gas introducing holes 1332. In other words, a plurality of the gas diffusion resistors 131 may be provided.

As such, according to the embodiment, the communication unit 13 is provided between the gas reduction chamber 11 and the gas measurement chamber 12 to separate the gas reduction chamber 11 and the gas measurement chamber 12 from each other. Then, by regulating the movement of the sample gas from the gas reduction chamber 11 to the gas measurement chamber 12 by the gas diffusion resistor 131 of the communication unit 13, the $SO_x$ concentration can be precisely measured in the gas measurement chamber 12.

(Second Solid Electrolyte Substrate 121 and Gas Measurement Chamber 12)

The second solid electrolyte 1213 is capable of supplying oxygen ion into the gas measurement chamber 12 and also capable of generating pump current therein. The second solid electrolyte 1213 is an oxygen ion conductive solid electrolyte. The second solid electrolyte 1213 is not particularly limited, but yttria-stabilized zirconia, calcia-stabilized zirconia, samarium-doped ceria or the like may be used, for example. Yttria-stabilized zirconia may be preferably used in view of oxygen ion conductivity and mechanical strength.

The power source 15 is connected to the third electrode 1214 and the fourth electrode 1211. Specifically, in this embodiment a positive electrode of the power source 15 is connected to the third electrode 1214 and a negative electrode of the power source 15 is connected to the fourth electrode 1211, respectively.

When voltage is applied to the third electrode 1214 and the fourth electrode 1211 by the power source 15, oxygen in atmosphere outside the $SO_x$ gas sensor 10 is ionized at the fourth electrode 1211 in accordance with a reaction of the following equation 2. At this time, magnitude of the voltage applied to the third electrode 1214 and the fourth electrode 1211 is not particularly limited as long as the reaction of the following equation 2 can occur.

$$\tfrac{1}{2}O_2 + 2e^- \rightarrow O^{2-} \qquad \text{(Equation 2)}$$

The ionized oxygen ion passes through the second solid electrolyte 1213 to be supplied into the gas measurement chamber 12. Then, in the gas measurement chamber 12, the $SO_2$ gas in the sample gas supplied into the gas measurement chamber 12 through the gas diffusion resistors 131 from the gas reduction chamber 11 is oxidized to $SO_3$ gas in accordance with a reaction of the following equation 3.

$$SO_2 + O^{2-} \rightarrow SO_3 + 2e^- \qquad \text{(Equation 3)}$$

Then, when oxygen ion is pumped from the fourth electrode 1211 to the third electrode 1214, pump current is generated in the second solid electrolyte 1213. Here, the total amount of the pump current corresponds to concentration of sulfur dioxide ($SO_2$) gas in the gas measurement chamber 12. Thus, the concentration of the $SO_x$ gas in the sample gas can be evaluated by measuring the pump current, in other words, variation of current that flows through the second solid electrolyte 1213 or variation of a resistance value of the second solid electrolyte 1213, caused by the pump current, by the ampere meter 16.

In order to measure the variation of the current value of the current that flows through the second solid electrolyte 1213 or the resistance value of the second solid electrolyte 1213, the ampere meter 16 is connected to the third electrode 1214 and the measurement electrode 1212. In other words, the third electrode 1214 also functions as a measurement electrode.

Structures of the third electrode 1214 and the fourth electrode 1211 are not particularly limited, however, at least the fourth electrode 1211 may be composed of metal capable of ionizing oxygen when voltage is being applied. For such metal, one or more metal selected from a group including platinum, palladium and iridium may be used, for example.

As the third electrode 1214 is provided in the gas measurement chamber 12 and the $SO_2$ gas is oxidized in the gas measurement chamber 12, the third electrode 1214 may be composed of oxidation catalyst capable of promoting the oxidation reaction of the $SO_2$ gas. As long as it is possible to promote the oxidation reaction, any catalyst may be used as the third electrode 1214. However, the third electrode 1214 may be composed of one or more material selected from metal, alloy and oxide including one or more material selected from a group including platinum, rhodium, ruthenium, palladium and iridium.

Position of the second solid electrolyte 1213 is not specifically limited, however, as the third electrode 1214, the fourth electrode 1211 and the measurement electrode 1212 and the like are provided on the second solid electrolyte 1213, the second solid electrolyte 1213 may be provided at a position where these electrodes are easily provided. Further, as the second solid electrolyte 1213 supplies the oxygen ion into the gas measurement chamber 12, the second solid electrolyte 1213 may be provided to face outside of the $SO_x$ gas sensor 10. For example, as illustrated in FIG. 1A, when the $SO_x$ gas sensor 10 has a structure in which the gas reduction chamber 11 is positioned above the gas measurement chamber 12, the first solid electrolyte 1132 and the second solid electrolyte 1213 may be symmetrically provided in an upper and lower direction with respect to the communication unit 13 as a center.

As illustrated in FIG. 1A, the third electrode 1214 is used as the measurement electrode connected to the ampere meter 16 and the measurement electrode 1212 is separately provided from the fourth electrode 1211 in this embodiment. However, alternatively, the fourth electrode 1211 may be used as a measurement electrode connected to the ampere meter 16 and a measurement electrode separately provided from the third electrode 1214 may be provided on the one surface of the second solid electrolyte 1213.

In this case as well, in order to promote the oxidation reaction of equation 3, an oxidation catalyst electrode may be provided in the gas measurement chamber 12. In particular, the third electrode 1214 may be composed of oxidation catalyst as explained above. When the third electrode 1214 is composed of the oxidation catalyst, voltage necessary for promoting the reactions of equation 2 and equation 3 may be applied between the third electrode 1214 and the fourth electrode 1211.

The shape of the $SO_x$ gas sensor 10 of the embodiment is not particularly limited, and may be various shapes such as a square pole shape, a columnar shape or the like. In particular, the shape of the $SO_x$ gas sensor 10 of the embodiment may be a columnar shape in view of processability.

The $SO_x$ gas sensor 10 of the embodiment may be composed of ceramics, for example. Specifically, the first wall portion 114, the second wall portion 123 and the substrate 1331 of the communication unit 13 of the $SO_x$ gas sensor 10 of the embodiment may be composed of various ceramics. Then, the $SO_x$ gas sensor 10 of the embodiment may be manufactured by stacking compacts of the second solid electrolyte 1213, the second wall portion 123, the substrate 1331 of the communication unit 13, the first wall portion 114 and the first solid electrolyte 1132 and the like in this order and baking them. At this time, difference in coefficients of thermal expansion (linear coefficients of expansion) of the compacts may be as small as possible. Thus, the first wall portion 114 and the second wall portion 123 may be composed of alumina ($Al_2O_3$), yttria-stabilized zirconia or the like. Further, the substrate 1331 of the communication unit 13 may be composed of yttria-stabilized zirconia or the like. The electrodes or wirings may be formed by printing metal paste after forming the ceramics compacts and before baking, for example.

Although in this embodiment, the first solid electrolyte substrate 113 and the first wall portion 114 or the second solid electrolyte substrate 121 and the second wall portion 123 are separately provided, respectively, the first solid electrolyte substrate 113 and the first wall portion 114 or the second solid electrolyte substrate 121 and the second wall portion 123 may be integrally formed. In other words, the first solid electrolyte 1132 and the first wall portion 114 may be integrally formed by an oxygen ion conductive solid electrolyte as described above. Similarly, the second solid electrolyte 1213 and the second wall portion 123 may be integrally formed by an oxygen ion conductive solid electrolyte as described above.

Further, alternatively, the first electrode 1133 and the second electrode 1131 may be provided on one surface and the other surface of the first wall portion 114, respectively. In this case, the first wall portion 114 may be composed of a material capable of exhausting oxygen in the gas reduction chamber 11 to outside the gas reduction chamber 11 and also capable of generating pump current therein. Similarly, the third electrode 1214 and the fourth electrode 1211 may be provided on one surface and the other surface of the second wall portion 123, respectively. In this case, the second wall portion 123 may be composed of a material capable of supplying oxygen ion into the gas measurement chamber 12 and also capable of generating pump current therein.

Shapes of the electrodes 1131, 1133, 1211, 1212 and 1214 are not particularly limited. For example, when the $SO_x$ gas sensor 10 has a columnar shape, each of the electrodes 1131, 1133, 1211, 1212 and 1214 may be formed as follows. Here, the first gas introducing hole 111 may be provided on a center axis of the first solid electrolyte 1132, in other words, on a center axis of the $SO_x$ gas sensor 10. Then, the first electrode 1133 having a disk form provided with an opening portion at its center concentrically with the first gas introducing hole 111 may be formed on the one surface of the first solid electrolyte 1132. At this time, the second electrode 1131 may have the same shape as the first electrode 1133 and may be formed on the other surface of the first solid electrolyte 1132.

The gas diffusion resistor 131 for flowing the $SO_2$ gas generated in the gas reduction chamber 11 to the gas measurement chamber 12 may be provided at the center of the substrate 1331 of the communication unit 13, in other words, on the center axis of the $SO_x$ gas sensor 10.

The shape of the third electrode 1214 provided in the gas measurement chamber 12 may be a circular shape, for example, in accordance with the shape of the $SO_x$ gas sensor 10. Further, the fourth electrode 1211 and the measurement electrode 1212 may be formed to have a circular shape in total. At this time, a slit may be provided between the fourth electrode 1211 and the measurement electrode 1212 so that they are electrically insulated.

According to the embodiment, as silver sulfate used in a conventional $SO_x$ gas sensor is not included, the $SO_x$ gas sensor 10 that is thermally and chemically stable can be provided.

Next, a method of detecting a gas of the embodiment is explained.

The method of measuring the concentration of the $SO_x$ gas of the embodiment may be performed as follows.

First, the method includes an oxidation step of oxidizing the noise gasses other than the $SO_x$ gas included in the sample gas.

The method further includes a first supplying step of supplying the sample gas, to which the oxidation step is performed, into the gas reduction chamber 11, and a reduction step of reducing the $SO_x$ gas in the sample gas supplied into the gas reduction chamber 11 while exhausting oxygen in the gas reduction chamber 11 to outside the gas reduction chamber 11.

The method further includes a second supplying step of supplying the sample gas, to which the reduction step is performed, into the gas measurement chamber 12 through the gas diffusion resistor 131 of the communication unit 13.

The method further includes a measuring step of measuring variation of a current value of current that flows through the second solid electrolyte 1213, that composes a part of a wall of the gas measurement chamber 12, or variation of a resistance value of the second solid electrolyte 1213 while supplying oxygen ion into the gas measurement chamber 12 through the second solid electrolyte 1213 to oxidize the $SO_2$ gas included in the sample gas to $SO_3$ gas in the gas measurement chamber 12.

As the sample gas is introduced into the gas reduction chamber 11 after the oxidation step, even when the sample gas originally includes the noise gasses such as hydrogen, carbon monoxide or the like, the noise gasses can be removed. Thus, the $SO_x$ gas can be selectively introduced into the gas reduction chamber 11 as the sample gas.

Then, by supplying the sample gas into the gas reduction chamber 11 in the first supplying step, and exhausting oxygen in the gas reduction chamber 11 to outside the gas reduction chamber 11 in the reduction step, the $SO_x$ gas in the sample gas is reduced. Specifically, the $SO_3$ gas included in the $SO_x$ gas is reduced to the $SO_2$ gas in accordance with the reaction of the above described equation 1.

Next, the sample gas mainly including the $SO_2$ gas generated in the reduction step is introduced into the gas measurement chamber 12 from the gas reduction chamber 11 through the gas diffusion resistor 131 of the communication unit 13. At this time, by regulating the movement of the gasses between the gas reduction chamber 11 and the gas measurement chamber 12 by the communication unit 13, the concentration of the $SO_x$ gas in the sample gas can be precisely measured.

Further, in the measuring step, oxygen ion is generated at the fourth electrode 1211 by applying voltage between the third electrode 1214 and the fourth electrode 1211 of the second solid electrolyte substrate 121 (equation 2). Then, oxygen ion is supplied into the gas measurement chamber 12 through the second solid electrolyte 1213.

Then, the sample gas in the gas measurement chamber 12, in other words, the $SO_2$ gas supplied from the gas reduction chamber 11 through the gas diffusion resistor 131, is oxidized by the oxygen ion supplied into the gas measurement chamber 12 to the $SO_3$ gas.

Here, in the measuring step, when the oxygen ion is supplied into the gas measurement chamber 12, a pump current is generated in the solid electrolyte 1213. As the total amount of the pump current corresponds to the concentration of sulfur dioxide ($SO_2$) introduced into the gas measurement chamber 12, the concentration of the $SO_x$ gas in the sample gas is evaluated by measuring variation of the current value of current that flows through the second solid electrolyte 1213 or the resistance value of the second solid electrolyte 1213, caused by the pump current. Thus, by measuring the variation of the current value that flows in the solid electrolyte 1213 or the resistance value of the solid electrolyte 1213, the concentration of the $SO_x$ gas in the sample gas is evaluated.

The above described method of measuring the concentration of the $SO_x$ gas may be performed by using the $SO_x$ gas sensor 10.

According to the embodiment, a $SO_x$ gas sensor that is thermally and chemically stable can be provided.

Although a preferred embodiment of the $SO_x$ gas sensor and the method of measuring the concentration of $SO_x$ gas has been specifically illustrated and described, it is to be understood that minor modifications may be made therein without departing from the spirit and scope of the invention as defined by the claims.

The present invention is not limited to the specifically disclosed embodiments, and numerous variations and modifications may be made without departing from the spirit and scope of the present invention.

What is claimed is:

1. An $SO_x$ gas sensor comprising:
   a gas reduction chamber in which $SO_x$ gas included in sample gas is reduced;
   a gas measurement chamber in which the concentration of the reduced $SO_x$ gas generated in the gas reduction chamber is measured while the reduced $SO_x$ gas is being oxidized;
   a first solid electrolyte composing a part of a wall of the gas reduction chamber and provided with
      a first gas introducing hole for introducing the sample gas into the gas reduction chamber,
      an oxidation part made of a material including an oxidation catalyst and provided in the first gas introducing hole for oxidizing noise gas other than the $SO_x$ gas included in the sample gas, and
      a reduction mechanism including a first electrode and a second electrode provided on the first solid electrolyte for reducing in the gas reduction chamber the $SO_x$ gas included in the sample gas after oxidation by the oxidation part;
   a communication unit provided between the gas reduction chamber and the gas measurement chamber to partition the gas reduction chamber and the gas measurement chamber and provided with
      a second gas introducing hole for introducing the reduced $SO_x$ gas into the gas measurement chamber from the gas reduction chamber, and
      a gas diffusion resistor provided in the second gas introducing hole; and
   a second solid electrolyte composing a part of a wall of the gas measurement chamber and provided with
      an oxidation mechanism including a third electrode and a fourth electrode provided on the second solid electrolyte for oxidizing in the gas measurement chamber the reduced $SO_x$ gas generated in the gas reduction chamber, and
      a measurement mechanism including a measurement electrode provided on the second solid electrolyte for measuring the concentration of the reduced $SO_x$ gas introduced into the gas measurement chamber from the gas reduction chamber and being oxidized in the gas measurement chamber.

2. The $SO_x$ gas sensor according to claim 1,
   wherein the first solid electrolyte is an oxygen ion conductive first solid electrolyte,
   wherein the first electrode is provided on one surface of the oxygen ion conductive first solid electrolyte, and
   wherein the second electrode is provided on another surface of the oxygen ion conductive first solid electrolyte and within the gas reduction chamber, the other surface being opposite to the one surface,
   wherein the second solid electrolyte is member an oxygen ion conductive second solid electrolyte,
   wherein the third electrode is provided on one surface of the oxygen ion conductive second solid electrolyte and within gas measurement chamber,
   wherein the fourth electrode is provided on another surface of the second solid electrolyte, the other surface being opposite to the one surface,
   wherein the measurement electrode is provided on the one surface or the other surface of the second solid electrolyte to be separated from the third electrode or the fourth electrode, respectively,
   the first solid electrolyte member being configured to exhaust oxygen in the gas reduction chamber to outside the gas reduction chamber through the oxygen ion conductive first solid electrolyte when voltage is being applied between the first electrode and the second electrode, and
   the second solid electrolyte member being configured to supply oxygen ion into the gas measurement chamber from outside the gas measurement chamber through the oxygen ion conductive second solid electrolyte when voltage is being applied between the third electrode and the fourth electrode to cause pump current.

3. The $SO_x$ gas sensor according to claim 1,
   wherein the oxidation part includes
      a porous ceramics, and
      one or more materials supported at a surface and inside the porous ceramics, each of the material including metal, alloy or oxide including one or more oxidation catalyst selected from a group including platinum, rhodium, ruthenium and palladium.

4. The $SO_x$ gas sensor according to claim 1,
   wherein the first gas introducing hole is a cylindrical open portion that penetrates the first solid electrolyte member, and
   wherein the second gas introducing hole is a cylindrical open portion that penetrates the communication unit, and the gas diffusion resistor is provided in the second gas introducing hole.

5. The $SO_x$ gas sensor according to claim 1,
   wherein the communication unit is provided with a plurality of the second gas introducing holes and the gas diffusion resistor is provided in each of the second gas introducing holes.

6. The $SO_x$ gas sensor according to claim 1,
   wherein the $SO_x$ gas sensor has a columnar shape.

7. The $SO_x$ gas sensor according to claim 1, wherein the oxygen ion conductive second solid electrolyte is composed of yttria-stabilized zirconia.

8. A method of measuring concentration of $SO_x$ gas included in sample gas, comprising:
   an oxidation step of oxidizing noise gas other than the $SO_x$ gas included in the sample gas;
   a first supplying step of supplying the sample gas after the oxidation step, into a gas reduction chamber;
   a reduction step of reducing the $SO_x$ gas included in the sample gas in the gas reduction chamber while exhausting oxygen in the gas reduction chamber to outside the gas reduction chamber;
   a second supplying step of supplying the sample gas after the reduction step, into a gas measurement chamber from the gas reduction chamber through a gas diffusion resistor; and
   a measuring step of measuring variation of a current value of current that flows through a solid electrolyte that composes a part of a wall of the gas measurement chamber or variation of a resistance value of the solid electrolyte, while supplying oxygen ion into the gas measurement chamber through the solid electrolyte and oxidizing $SO_2$ gas included in the sample gas to $SO_3$ gas in the gas measurement chamber.

* * * * *